United States Patent
Katus et al.

(10) Patent No.: US 6,376,206 B1
(45) Date of Patent: Apr. 23, 2002

(54) SPECIFIC ANTIBODIES TO TROPONIN T, THEIR PRODUCTION AND USE IN A REAGENT FOR THE DETERMINATION OF MYOCARDIAL NECROSIS

(75) Inventors: Hugo Katus; Anneliese Borgya; Klaus Hallermayer; Siegfried Looser, all of Manheim (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 08/487,540

(22) Filed: Jun. 7, 1995

Related U.S. Application Data

(63) Continuation of application No. 08/028,650, filed on Mar. 8, 1993, now abandoned, which is a continuation of application No. 07/513,747, filed on Apr. 24, 1990, now abandoned.

(30) Foreign Application Priority Data

Apr. 25, 1989 (DE) ............................................. 39 13 568
Jul. 12, 1989 (DE) ............................................. 39 22 873

(51) Int. Cl.$^7$ .......................... G01N 33/53; C12N 5/06; C12N 11/00; C12P 21/08
(52) U.S. Cl. .................... 435/7.92; 435/7.93; 435/7.94; 435/7.9; 435/174; 435/328; 435/975; 435/188; 530/388.25; 530/391.3
(58) Field of Search .......................... 435/7.1, 7.5, 7.9, 435/7.92, 7.93, 7.94, 70.21, 188, 240.27, 975, 174, 328; 436/531, 532, 547, 548, 811; 424/85.8; 530/387.1, 388.1, 389.1, 391.1, 391.3, 391.5, 388.25

(56) References Cited

PUBLICATIONS

Katus et al., "Proteins of the Troponin Complex", *Laboratory Medicine,* vol. 23, No. 5, (1992), pp. 311–317.*
Gerhardt et al., S–Troponin T in Suspected Ischemic Myocardial Injury Compared with Mass and Catalytic Concentrations of S–Creatinine.
Kinase Isoenzyme MB, *Clin. Chem.* vol. 37, No. 8, pp. 1405–1411 (1991).
Katus et al., "Development and In Vitro Characterization of a New Immunoassay of Cardial Troponin T", *Clin Chem.,* vol. 38, No. 3, pp. 386–393, (1992).
Katus et al., "Diagnosis of Acute Myocardial Infarction by Detection of Circulating Cardiacmyosin Light Chains," *The American Journal of Cardiology,* vol. 54, (1984), pp. 964–970.*
Kabat, Elvin A. "Basic Principles of Antigen–Antobody Reactions", in Methods in Enzymology, Vunakis et al., Eds. Academic Press, New York, pp. 31–35, (1980).*
Maurer et al., "Proteins and Polypeptides as Antigens", in Methods in Enzymology, Vunakis et al., Eds, Academic Press, New York, pp. 64–67.*
Buckland, R.M., "Strong Signals From Streptauipin–Biotin", Nature, vol. 320, pp. 557–558, (1986).*
Sevier et al., Clin. Chem. vol. 27, No. 11, pp. 1797–1806, (1981).*
Cummins et al., American Heart Journal, vol. 113, No. 6, pp. 1333–1344, (1987).*
Journal of Molecular and Cellular Cardiology, vol. 19, No. 7, Jul. 1987.
Chemical Abstracts, vol. 107, No. 9, Aug. 31, 1987.
Chemical Abstracts, vol. 103, No. 13, Sep. 30, 1985.
Chemical Abstracts, vol. 102, No. 15, Apr. 15, 1985.
Chemical Abstracts, vol. 102, No. 7, Feb. 18, 1985.
Mair et al., Crit. Rev. Clin. Lab. Sci. 29 (1992) 31–57, "Cardiac Troponin T in the Diagnosis of Myocardial Injury".
Hamm et al., N. Engl. J. Med. (1992) 327(3) 146–149, "The Prognostic Value of Serum Troponin T in Unstable Angina".
Katus et al., Circulation 83 (1991) 902–912, "Diagnostic Efficiency of Tropinin T Measurements in Acute Myocardial Infarction".
Mächler et al., 2. Alpe–Adria Congr., Graz, Austria, Nov. 12–14, 1992, "Diagnostic efficiency of Troponin T versus CK–MB/CPK measurements in unstable angina pectoris patients prior to and during cabg".
Gerhardt et al., Clin Chem. vol 38, No. 6, (1992) pp. 1195–1196, "S–Troponin–T as a Marker of Ischemic Myocardial Injury".
Ravkilde et al., Clin Chem. vol. 38, No. 6, (1992) p. 1091, "The Nordic Troponin–T Multicenter Study Group, Identifying a Possible High–Risk Group in Patients Suspected of Acute Myocardial Infarction Based on Troponin–T in Serum".
Katus et al., JACC vol. 11, No. 3, Mar. 1988, pp. 487–493, "Circulating Cardiac Myosin Light Chains in Patients With Angina at Rest: Identification of a High Risk Subgroup".
Dillon et al., Arch. Intern. Med., vol. 142, Jan 1982, pp. 33–38, "Diagnostic Problem in Acute Myocardial Infarction: CK–MB in the Absence of Abnormally Elevated Total Creatine Kinase Levels".
Benhorin et al., JACC vol. 15, No. 6, May 1990, pp. 1201–1207, "The Prognostic Significance of First Myocardial Infarction Type (Q Wave Versus Non–Q Wave) and Q Wave Location".

(List continued on next page.)

*Primary Examiner*—Mary E. Ceperley
*Assistant Examiner*—My-Chau Tran
(74) *Attorney, Agent, or Firm*—Marilyn L. Amick; Roche Diagnostics Corporation

(57) ABSTRACT

An immunoassay for the determination of myocardial necroses using antibodies to troponin T and a binding partner B for troponin T or for the an antibody, whereby either the antibody or the binding partner B is labelled with a determinable group. The immunological complex formed which contains the determinable group is isolated by separation of the phases and the determinable group is determined in one of the phases. Furthermore, monoclonal and polyclonal antibodies to troponin T are described with a cross-reactivity of less than 5% to skeletal muscle troponin T and less than 2% to troponin I and other myofibrillar proteins.

24 Claims, 3 Drawing Sheets

OTHER PUBLICATIONS

Figure 1:
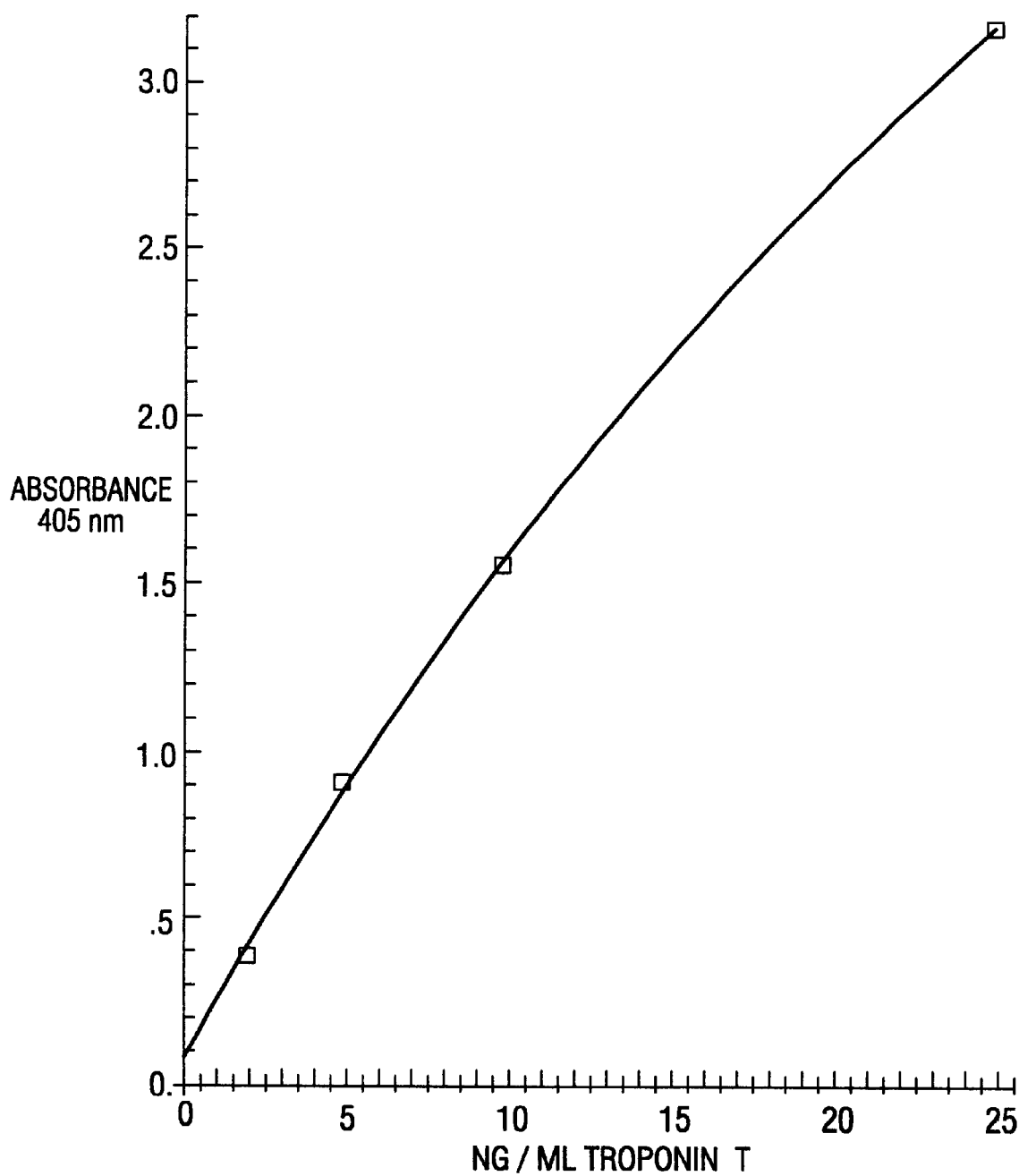

White et al., Am. J. of Cardiol., vol. 55, Jun. 1985, pp. 1478–1484, "Diagnostic and Prognostic Significance of Minimally Elevated Creatine Kinase–MB in Suspected Acute Myocardial Infarction".

Goldberg et al., Am. Heart J., vol. 113, No. 2, Part 1, pp. 273–279, "Non–Q Wave Myocardial Infarction: Recent Changes in Occurrence and Prognosis—a CommunityWide Perspective" (1987).

Cummins et al., Eur. J. of Clin. Investigation, vol. 17, No. 4, (1987), pp. 317–324, "Comparison of serum cardiac specific troponin–I with creatine kinase, creatine kinase–MB isoenzyme, tropomyosin, myoglobin and C–reactive protein release in marathon runners: cardiac or skeletal muscle trauma".

Mesnard et al., FEBS, vol. 328, No. 1.2, (1993), pp. 139–144, "Molecular cloning and developmental expression of human cardiac troponin T".

Sabry et al., J. Muscle Res. and Cell Motility, vol. 12, pp. 262–270 (1991), "Identification of and pattern of transitions of cardiac, adult slow and slow skeletal muscle–like embryonic isoforms of troponin T in developing rat and human skeletal muscles".

Gahlmann et al., J. Mol. Biol., vol. 201, (1988), pp. 370–391, "Differential Expression of Slow and Fast Skeletal Muscle Troponin C".

Pearlstone et al., J. Biol. Chem., vol. 261, No. 36, (1986), pp. 16795–16810, "Amino Acid Sequence of Rabbit Cardiac Tropinin T".

Briggs et al., J. Mol. Biol. vol. 206, (1989), pp. 245–249, "N–Terminal Amino Acid Sequences of Three Functionally Different Troponin T Isoforms from Rabbit Fast Skeletal Muscle".

\* cited by examiner

SPECIFIC ANTIBODIES TO TROPONIN T, THEIR PRODUCTION AND USE IN A REAGENT FOR THE DETERMINATION OF MYOCARDIAL NECROSIS

This application is a continuation of application Ser. No. 08/028,650 filed Mar. 8, 1993, now abandoned which was a continuation of 07/513,747 filed Apr. 24, 1990 now abandoned.

The invention concerns specific antibodies to cardiac muscle troponin T, their production and use in an immunological reagent for the determination of myocardial necrosis.

The myofibrils of the striated muscle consist of two protein filaments which act in combination, the thick filaments have myosin as their main component and the thin filaments contain actin, tropomyosin and troponins. Troponin, a regulatory structural protein, aggregates to a complex in the cells and consists of three different proteins:

Troponin C (MW 18000) which binds calcium ions

Troponin I (MW 24000) a sub-unit binding actin

Troponin T (MW 37000) which complexes with tropomyosin.

The comparable nomenclature has historical reasons since originally the complex as such was purified and was looked upon as a single protein and denoted troponin. Later it was proven that troponin really consists of three different proteins. This nomenclature was then retained because of the spacial relationship between the proteins on the thin filament of the contractile apparatus and because of their cooperation with respect to the regulation of muscle contraction. They are, however, three different proteins which are functionally related to the other proteins of the contractile apparatus such as myosin or actin but which have different amino acid sequences.

During long lasting severe ischaemia or muscle cell necrosis troponin I reaches the blood plasma and is thus a parameter for such diseases which can also be used for diagnosis and monitoring analogous to the known infarction enzymes CK, CK-MB, GOT and LDH.

It has been shown that the determination of CK and CK-MB is not absolutely specific for an infarction and is only increased in the serum 80 to 90 hours after the infarction. GOT and LDH are also not specific for cardiac muscle since increased amounts are also found in the blood in many other diseases.

The disadvantage of a determination of cardiac troponin I is that normally serum already contains concentrations of troponin I at a level of 10 ng/ml (cf. B. Cummins, J. Mol. Cell. Card. 19 (1987), 999–1010 and B. Cummins, Clin. Invest. 113 (1987) 1333–1344). It turns out that a biphasic serum concentration occurs in a transmural infarction on average, troponin I was increased from the 4th to the 168th hour after the onset of pain in 37 patients with acute transmural infarction. Similar results were obtained in an animal model. Accordingly it follows that for troponin I the 10th to 50th hour after the occurrence of an infarction is the time interval for the absolute diagnostic sensitivity. Thus, apart from the limited sensitivity, due to variable serum levels of troponin I the clinically important monitoring for 10 days and more after the occurrence of the infarction cannot be achieved by the determination of troponin I.

It was therefore the object of the present invention to eliminate these disadvantages and to provide a method for the determination with which monitoring is possible for at least 150 hours (duration of absolute diagnostic sensitivity) in myocardial infarctions and other injuries to the cardiac muscle.

This object is achieved by a method for the determination of myocardial necrosis according to the immunoassay principle which is characterized in that a serum or plasma sample is incubated with at least one antibody to troponin T and a binding partner B for troponin T or for the antibody, in which either the antibody to troponin T or the binding partner B is labelled with a determinable group, the immunological complex which thereby forms is isolated and the determinable group is determined in the isolated or in the remaining phase as a measure for troponin T from the sample.

The binding partner B has to bind to the antibody to troponin T or to troponin T. B can be for example a second antibody to troponin T or troponin T from humans or animals or an analogue thereof which is bound by the antibody.

The sample is preferably incubated with an antibody to troponin T and a conjugate of a further antibody to troponin T and a determinable group, the immunological complex formed is isolated by separation of the phases and the determinable group is determined in one of the phases.

It is furthermore preferred to incubate the sample with an antibody to troponin T and a conjugate of troponin T and a determinable group, to isolate the immunological complex formed by separation of the phases and to determine the determinable group in one of the phases.

Surprisingly, it turned out that a significantly higher sensitivity can be obtained by a troponin T immunoassay in the determination of myocardial necroses (such as e.g. by cardiac infarction, ischaemia or angina pectoris) than by the determination of other parameters such as CK, CK-MB, GOT, LDH or troponin I. As established by the inventors the reason for this is that in contrast to other proteins of the contractile apparatus no serum concentration can be measured for troponin T up to the detection limit of the test (0.25 ng/ml) in normal patients (who have not suffered myocardial necroses).

This is particularly surprising since, because of the functional relationship between the troponins, a similar serum concentration to that for troponin I would be expected for troponin T. Furthermore, the serum concentration curve of troponin T differs significantly, for example in a transmural infarction, from the curve for troponin I. In contrast to troponin I the curve of the time course is in three phases instead of two phases and troponin T is found to be increased on average for up to 300 hours after the onset of pain. The time interval for absolute diagnostic sensitivity lasts from the 6th to the 195th hour. The time interval for the absolute diagnostic sensitivity is thus nearly four times as long as that known for troponin I.

All common immunoassays are in principle suitable for the immunological method of determination according to the present invention such as radioimmunoassay, enzyme-immunoassay, fluorescence immunoassay etc. Furthermore, all variants of these procedures such as competitive immunoassay, IEMA procedure etc. are applicable. A sandwich test has proven to be particularly effective for the determination of troponin T. In this test procedure an immobilized antibody to troponin T and a conjugate of an antibody to troponin T and a determinable group is used. The different variants of this test method as well as details for carrying out these procedures are described at length in the literature. However, other immunological methods of determination are also possible using the antibodies according to the present invention such as those described e.g. in the German patent application DE-A 38 34 766 and/or DE-A 38 22 750.

Within the scope of the invention an antibody is understood as a complete antibody, chimeric antibody, bivalent antibody or fragments thereof. The troponin T antibodies used can be polyclonal or monoclonal. Monoclonal antibodies are preferably used.

In the sandwich test the sample solution is incubated with at least two antibodies to troponin T as a preferred embodiment. The first antibody thereby mediates the binding to the solid phase. For this, this antibody can either be bound directly or via a spacer to the solid phase or it can be present in a soluble form and only be immobilized after the immunological reaction has been carried out. The second antibody can either be labelled directly with a certain group or it can be bound to the determinable group by a functional bond. For this the antibody can be bound to one partner of a specific binding pair and the determinable group can be bound to the other partner of the specific binding pair. A complex which contains the second antibody as well as the determinable group then forms during the reaction. The binding of the first antibody to the carrier (immobilization) is carried out according to methods known to the expert by adsorptive, chemical binding or by functional binding via a specific binding pair. In this case one partner of the binding pair is immobilized while the other partner is chemically bound to the antibody. The antibody can then be immobilized before or during the immunological determination reaction via this binding pair. Examples of such binding pairs are biotin-streptavidin/avidin, hapten-antibody, antigen-antibody, sugar-lectin, hapten-binding protein.

The competitive test is a further preferred variant of the test. In this case an antibody to troponin T which is immobilized either before or during the determination and a conjugate of troponin T and a determinable group are used.

Materials can be used as carrier materials for the immobilization of the antibodies according to the present invention or for the immobilization of troponin T such as e.g. tubes, plastic cuvettes, microtitre plates, beads or plastic microcarriers, such as polystyrene, vinylpolymers, polypropylene, polycarbonate, polysaccharides, silicons, rubber or treated glass (cf. e.g. E. T. Maggio "Enzyme Immunoassay" CAC. Press, Florida (1980), in particular pages 175178, EP-A-063064, Bioengineering 16 (1974), 997–1003, C. J. Senderson and D. V. Wilson, Immunology 20 (1971), 1061–1065). In particular a carrier material, especially polystyrene, coated with avidin or streptavidin is used and is preferably prepared as described in EP-A-0269092. The binding partner B likewise contains either troponin T or an analogue thereof or a monoclonal antibody capable of specific binding to troponin T and is labelled. The usual agents for the respective determination method are suitable for the labelling. Thus, radioisotopes such as $^{57}$Co are used for the labelling in a radioimmunoassay. All enzymes which are usually used for an enzyme-immunoassay are suitable, for example, peroxidase or 0-galactosidase. The common fluorescent groups are suitable as a label for a fluorescence immunoassay. Details of these different test methods and variants of the procedures are known to the expert. The binding of the label to troponin T or to the antibody can be carried out in an analogous manner to the binding to the solid phase i.e. covalently or via a specific binding pair.

The antibody or troponin T is covalently bound to one of the above-mentioned binding partners according to methods known to the expert, for example via carbodiimide and hydroxysuccinimide.

Peroxidase (POD) is preferably used as the enzyme label.

A further embodiment of the invention is a process for the production of polyclonal antibodies capable of specific binding to cardiac muscle troponin T, whose cross-reaction to human skeletal muscle troponin T is less than 5% and is less than 2% to troponin I and other myofibrillar proteins. The process consists in immunizing experimental animals, preferably sheep, with human cardiac muscle troponin T in combination with an adjuvant over several months (preferably 4–6 months) with at least four immunizations at intervals of four to six weeks, isolating the raw serum and purifying it immunosorptively.

A further embodiment of the invention is a process for the production of monoclonal antibodies capable of specification binding to cardiac muscle troponin T whose cross-reaction to human skeletal muscle troponin T is less than 5% and is less than 2% to troponin I and other myofibrillar proteins. The process is characterized in that experimental animals, preferably in-bred mice, are immunized intraperitoneally over several months with human cardiac muscle troponin T in combination with an adjuvant with at least four immunizations at intervals of four to six weeks, B lymphocytes are isolated and fused with a permanent myeloma cell line, the clones are isolated and the antibodies are isolated from them.

Aluminium hydroxide together with Bordatella pertussis or Freund's adjuvant is preferably used as the adjuvant.

The primary cultures of hybrid cells obtained during the fusion according to the well-known procedure of Köhler and Milstein (Nature 256 (1975), 495–497) are cloned in the usual way e.g. using commercial cell sorters or by "limiting dilution". Those cultures are used further which react positively to isolated cardiac muscle troponin T and to cardiac muscle troponin T in the serum of patients and which react negatively to troponin T from skeletal muscle. Hybridoma cell lines are obtained in this way which produce the monoclonal antibodies according to the present invention. These cell lines can be cultured according to known methods and the monoclonal antibodies produced therefrom can be isolated.

Examples of hybridoma cell lines obtained in this was are clone 7.1 A 12.2-22 (ECACC 89060901) and clone 8.1 F 6.7-2 (ECACC 89030308). The cell lines are deposited under their respective quoted numbers at the European Collection of Animal Cell Cultures, PHLS Centre for Applied Microbiology & Research, Porton Down, Salisbury, Wilts. SP4, OJG, GB. on Jun. 9, 1989 and Mar. 3, 1989, respectively, The polyclonal or monoclonal antibodies thus obtained are distinguished by their low cross-reactivity to human skeletal muscle troponin T which is less than 5% and preferably below 2% and by a cross-reactivity to troponin I and other myofibrillar proteins of less than 2%. The polyclonal and monoclonal antibodies according to the present invention are especially suitable for the specific determination of myocardial necrosis in a sample such as serum or plasma. The antibodies can be used as such for these methods of determination or as chimeric antibodies or as fragments thereof, for example, Fab fragments which have the corresponding immunological properties. The term antibody is therefore understood to indicate complete antibodies as well as fragments thereof.

The following Examples and Figures elucidate the invention further without being limited by them. Percentages refer to percent by weight.

FIG. 1 Standard curve for troponin T assay.

Figure 2:
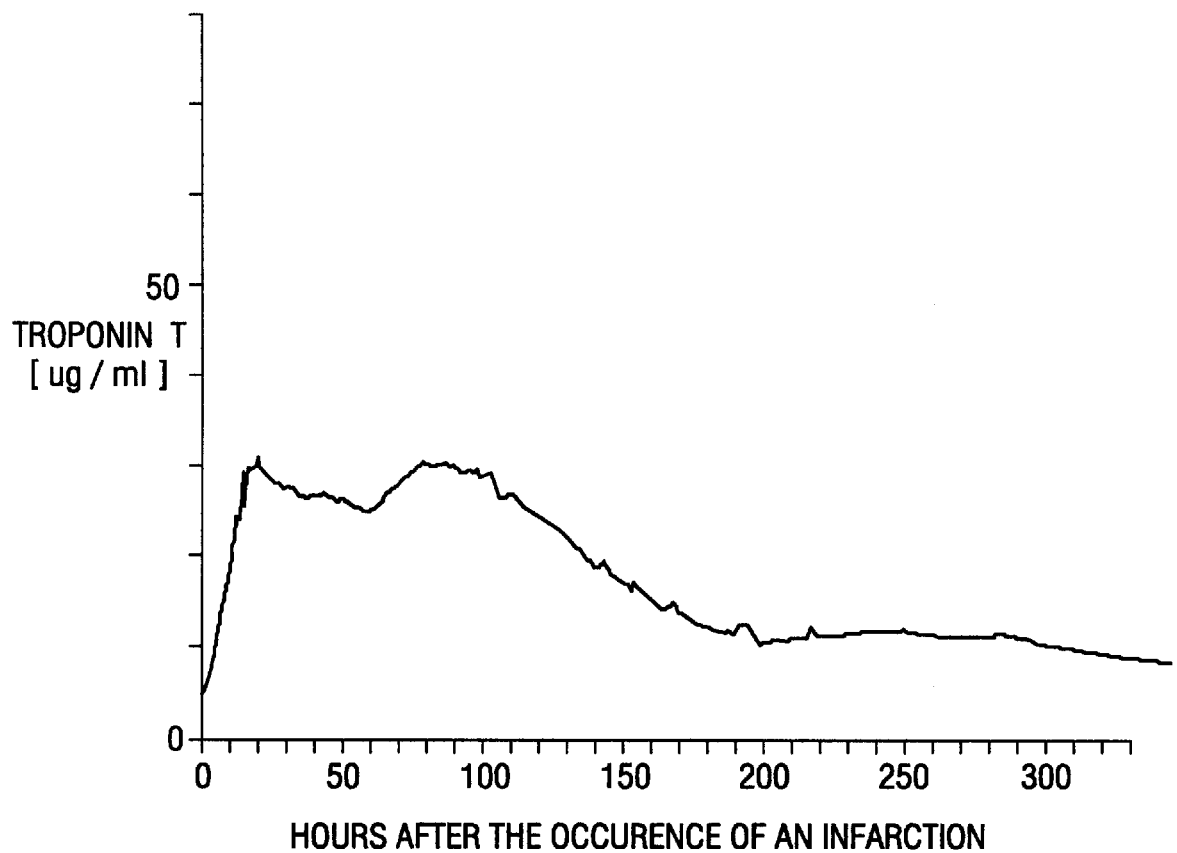

FIG. 2 Mean serum concentration of troponin T for 52 patients with transmural myocardial infarction.

Figure 3:
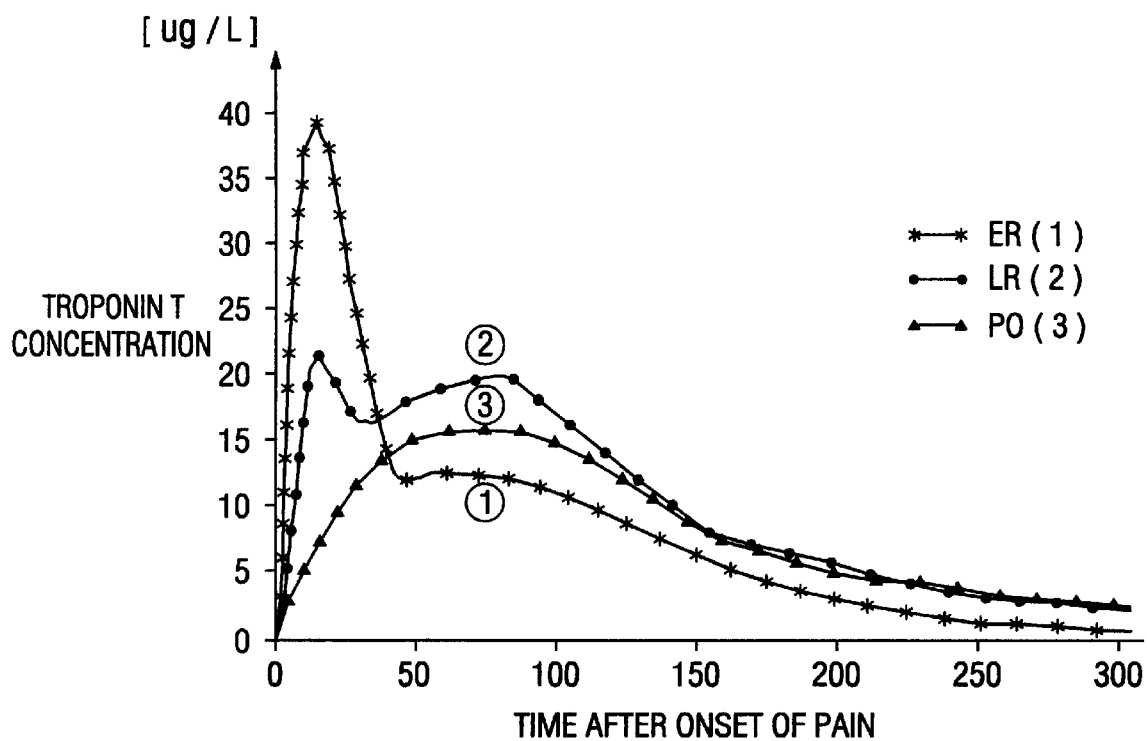

FIG. 3 Smoothed scatter plot by local weighted regression smoothing of relative increase of troponin T concentrations in serum in 20 patients with infarct reperfusion<3.5 hours after onset of pain (ER), 20 patients with reperfusion>3.5 hours after onset of pain (LR) and 24 patients with non-reperfused infarction (PO). Note the strikingly early troponin T release in successfully reperfused infarction.

EXAMPLE 1

Isolation of Troponin T

Buffer 1:
  0.05 mol/l Tris/HCl, Ph 7.0
  0.05 mol/l KCl
  10 ml/l Triton X 100
  2 mmol/l EDTA
  0.5 mmol/l DTT (dithiothreitol)
  0.02% sodium azide
  2 mmol/l PMSF (phenylmethylsulphonyl fluoride)
  5 mmol/l -aminocaproic acid
  2.5 ml Trasylol/l
  0.2 mg Pepstatin/l
Buffer 2:
  0.05 mol/l Tris/HCl, pH 7.0
  1 mol/l KCl
  5 mol/l urea
  2 mmol/l EDTA
  0.02% sodium azide (w/v)
Buffer 3:
  5 mmol/l potassium phosphate, pH 7.3
  2 mol/l urea
  0.6 mol/l KCl
  0.5 mmol/l DTT
  0.02% sodium azide (w/v)Buffer 4:
  0.05 mol/l Tris/HCl, pH 7.8
  6 mol/l urea
  0.01 mol/l NaCl
  2 mmol/l EDTA
  0.5 mmol/l DTT
  0.02% sodium azide (w/v)

300 g tissue (left ventricle without valves and vessels) is cut up into small pieces and homogenized intermittently in a mixer in a five-fold volume of buffer 1 for a maximum of 1 minute at 4° C. The insoluble component is centrifuged down at 27500 g for 15 min at 4C and the pellet is washed with 1 buffer 1 until the supernatant is completely clear.

The pellet is taken up in a 5–6 fold volume of buffer 2 and stirred for 3–4 hours at 4° C. It is centrifuged at 27500 g for 15 min at 4° C.

5 mmol/l ATP is added to the supernatant (final concentration after addition of ammonium sulphate) and brought to 35% ammonium sulphate by addition of ammonium sulphate solution saturated at 4° C./2 mmol/l EDTA in which the ammonium sulphate solution was previously neutralized with KOH. It is incubated overnight at 4C while stirring gently. Subsequently the precipitate is centrifuged down at 27500 g for 20 min at 4C.

The supernatant is brought to a 45% saturation with ammonium sulphate by addition of solid ammonium sulphate, stirred for 45 min at 4C and centrifuged down. The 35–45% ammonium sulphate precipitate contains troponin T and is processed further. The pellet is taken up in 25 ml buffer 3 (OD 280 nm should be between 1.5 and 2) and dialyzed against buffer 3 at 4C during which the buffer is changed at least twice.

The dialyzed solution is loaded onto a hydroxylapatite column (Biogel HTP, loaded with ca 25 mg protein/50 ml column volume, flow rate: 1 column volume/hour), rewashed with 4–5 column volumes of buffer 3 and eluted within 20 hours at one column volume/hour with a gradient of 5 mmol/l to 55 mmol/l potassium phosphate in buffer 3. The fractions containing troponin T are determined using SDS-page (gel gradient 5–25 pooled and dialyzed against buffer 4.

The dialyzed solution is loaded onto a column (DEAE SERVACEL™ SS23, column volume 20–30 ml, flow rate: 1 column volume/hour), re-washed with 3 column volumes of buffer 4 and eluted within 20 hours at one column volume/hour with a gradient of 0.01 mol/l to 0.25 mol/l NaCl in buffer 4. Troponin I appears in the eluate. Troponin T and troponin C elute separately. The fractions containing troponin T are pooled according to the SDS-page, re-dialyzed against buffer 4 and frozen for further use at −20° C. Ca. 6–8 mg troponin T are obtained from 300 g muscle.

EXAMPLE 2

Isolation of Monoclonal Antibodies to Human Troponin T

Balb/c mice, 8–12 weeks old, are immunized intraperitoneally with 100 Mg troponin T (isolated from human cardiac muscle according to Example 1) with complete Freund's adjuvant. After 6 weeks three further immunizations are carried out at 4-week intervals in each of which 50 mg troponin T, adsorbed to aluminium hydroxide and Bordatella pertussis are administered intraperitoneally. One week after the last immunization a blood sample is taken and the antibody titre is determined in the serum of the experimental animals.

If the immunization is positive, fusion is carried out. Four days, three days and two days before the fusion they are each again immunized intravenously with 100 mg troponin T in PBS (=phosphate buffered saline).

For the fusion $1\times10^8$ spleen cells of an immunized mouse are mixed with $2\times10^7$ myeloma cells (P3x63Ag8653, ATCC-CRL 8375) following Galfre (Methods in Enzymology, 73, 1981, p. 3) and subsequently centrifuged for 10 minutes (300 g, 4° C.). The cells are washed with serum-free culture medium and centrifuged again at 400 g. The supernatant is aspirated and 1 ml 50% PEG solution (MW 4000, Merck Company) is added to the cell sediment. Afterwards it is slowly diluted to 20 ml in 15 minutes at room temperature with RPMI 1640 medium (RPMI= Rosewell Park Memorial Institute) without fetal calf serum (FCS). Afterwards the cell suspension is centrifuged at 400 g for 10 minutes and the cell sediment is taken up in selection medium (RPMI 1640, 10% FCS, hypoxanthine 100 mmol/l, azaserine 1 mg/ml). For growth factors HECS (Human Endothelial Culture Supernatant) (Costar Company, No. 6110) is used as a feeder cell substitute.

The fused cells are plated on 24 well plates (Nunc Company) at $5\times10^4$ cells per well. Growth of clones is visible after 7–10 days. The culture supernatant of the primary cultures is tested by an ELISA procedure described in Example 3. The primary cultures which contain the antigen-specific antibodies are cloned further using a fluorescence activated cell sorter on 96-well cell culture plates (Nunc Company). HECS is used as a feeder cell substitute (see above).

In this way both the hybridoma cell lines clone 7.1A12.2-22 and 8.1F6.7-2 could be isolated which are deposited at the depositary institution ECACC (European Collection of Animal Cell Cultures) under the deposit numbers.

ECACC 89060901 Clone 7.1A12.2-22) and

ECACC 89030308 Clone 8.1F6.7-2)

In order to produce ascites, $5 \times 10^6$ hybridoma cells are injected intraperitoneally into Balb/c mice which have been pre-treated once or twice with 0.5 ml Pristan. After 2–3 weeks ascites fluid can be obtained from the abdomen of the mice. The antibodies can be isolated from this in the usual way. These monoclonal antibodies are directed specifically towards human cardiac muscle troponin T and show no or only slight cross-reactivity with troponin T from skeletal muscle. In the following they are denoted MAB 7.1A12.2-22 (from clone 7.1A12.222) or MAB 8.1F6.7-2 (from clone 8.1F6.7-2). Both the monoclonal antibodies belong to the subclass IgGl/kappa.

EXAMPLE 3

Screening Test for Antibodies to Human Cardiac Muscle Troponin T

In order to determine the presence and specificity of antibodies to troponin T in the serum of immunized mice, in the culture supernatant of the hybrid cells or in ascites fluid an ELISA procedure is used as the basis for the test: Microtitre plates are coated for 1 hour at room temperature with 10 μg/ml polyclonal antibody (IgG) to human troponin T from sheep (purified immunosorptively, no cross-reaction with skeletal muscle troponin T, cross-reaction with cardiac muscle troponin T, preparation according to Example 7) in coating buffer (0.2 mol/l sodium carbonate/sodium bicarbonate ph 9.39). The re-coating is carried out for 20 minutes with 0.9% sodium chloride solution and 1% bovine serum albumin. Afterwards they are washed with washing buffer (0.9% sodium chloride solution). The incubation of the antigen, purified human troponin T 1 μg/ml or native troponin T i.e. infarction serum (diluted 1:2), is carried out at room temperature for 1 hour with shaking using 100 μl per well. Then they are washed again twice with washing buffer. The samples are incubated at room temperature for 1 hour with shaking using 100 μl per well. They are then washed again twice with washing solution. This is followed by a further incubation for 1 hour at room temperature with shaking with 100 μl of 25 mU of a PAB<M-Fcg>S-Fab (IS)-peroxidase conjugate per well. (PAB<M-Fcg>S-Fab (IS)=Fab fragment of a polyclonal anti-mouse Fc antibody from sheep which was purified immunosorptively). The peroxidase activity is determined in the usual manner (for example with ABTS for 30 minutes at room temperature, the difference in absorption is read in mA at 405 nm) after a washing step with washing buffer.

EXAMPLE 4

Determination of the Cross-reactivity with Human Skeletal Muscle Troponin T

The procedure is carried out as described in Example 3. At first the reactivity of cardiac muscle troponin T is determined. Then the antigen to be tested for crossreaction (skeletal muscle troponin T) is added in increasing concentrations to the respective monoclonal antibody.

Subsequently the cross-reactions are calculated according to the following formula:

$$\frac{C(\text{cardiac muscle troponin } T)}{C(\text{skeletal muscle troponin } T)} \times 100 \text{ cross-reaction}$$

C=concentration of the antigen which is necessary in order to reach 50% of the maximum signal.

EXAMPLE 5

Determination of the Epitope Specificity

A microtitre plate is coated for 1 h at room temperature or overnight at 4C with 10 Mg/ml polyclonal sheep antibody to the Fcg region of a mouse antibody in 0.2 mmol/l carbonate buffer, ph 9.6. Afterwards it is re-coated for 20 min with incubation buffer (0.9% sodium chloride solution and 1% bovine serum albumin) and then washed with washing buffer (0.9% sodium chloride solution, 0.05% Tween 20). Subsequently 100 41 of a monoclonal antibody (MAB 7.1A12. 2-22, MAB 1), 10 Mg/ml in incubation buffer (0.9% sodium chloride solution containing 1% bovine serum albumin), is added and incubated for 1 hour at room temperature with shaking.

A second monoclonal antibody (MAB 8.1F6.7-2, MAB 2) which is present as a peroxidase conjugate is preincubated in solution (100 mu/ml) at room temperature with the antigen (1 Mg/ml cardiac muscle troponin T).

After the incubation of the plate with MAB 1 excess antibody is removed by washing. The plate is afterwards re-coated with 1% mouse normal serum in incubation buffer. 100 μl of the pre-incubated troponin T/MAB 2 peroxidase complex is put on the plate and incubated for 1 hour at room temperature with shaking. The bound peroxidase activity is visualized using ABTS as substrate. If the MAB 2 recognizes the same or an overlapping epitope as MAB 1 no pairs form between MAB 1/troponin TMAB 2 and consequently a substrate reaction occurs. The results obtained show that both the monoclonal antibodies 7.1A12.22 and 8.1F6.7-2 are directed towards different epitopes of the cardiac muscle troponin T antigen.

EXAMPLE 6

Enzyme-immunoassay for the Determination of Troponin T According to the ELISA Principle Reagent 1

1.25mg/ml biotinylated MAB 7.1A12.2-22 (preparation analogous to J. H. Peters et al., Monoklonale Antikörper, Springer Verlag, Berlin, 1985, pages 209–212). 10 mmol/l citrate buffer 47 mmol/l phosphate buffer, pH 6.3 50 mu/ml conjugate of peroxidase and monoclonal antibody 8.1F6.7-2 (prepared analogous to M. B. Wilson, P. K. Nakane (1987) in Immunofluorescence and Related Staining Techniques (W. Knapp, K. Kolubar, G. Wick eds.) pp. 215–224, Elsevier/North Holland, Amsterdam, the value for the activity relates to peroxidase).

Reagent 2

100 mmol/l phosphate-citrate buffer, pH 4.4 3.2 mmol/l sodium perborate 1.9 mmol/l ABTS (2,21-azino-di-[ethyl benzthiazoline-sulphonate(6)]) Human sera which are supplemented with 3, 5, 10 or 25 ng/ml troponin T are used as samples.

The reaction is carried out using polystyrene tubes coated with streptavidin (preparation according to EP-A-0269092).

Procedure for the determination:

0.2 ml sample is incubated for 60 min at 20–25° C. in a tube with 1 ml Reagent 1. It is aspirated and washed twice with tap water. Subsequently Reagent 2 is added, incubated for 30 min at 20–25° C. and the absorbance is determined in a photometer at 420 nm.

By this means a standard curve (FIG. 1) is obtained with which the troponin T concentration of patient samples can be determined.

EXAMPLE 7

Isolation and Purification of Polyclonal Antibodies to Cardiac Troponin T

Sheep are initially immunized with 55 41 of a solution of 0.1 mg/ml human cardiac muscle troponin T in complete Freund's adjuvant (CFA). Further immunizations are carried out on the 7th, 14th and 30th day. Subsequently they are immunized every 30 days. 28 41 of a 0.05 mg/ml troponin T solution in CFA is used for each of these subsequent immunizations. The raw serum is obtained after 6 months.

15 g AEROSIL™ agent (porous silica)(Producer: Degussa) is added to 1 1 raw serum, stirred for 1 hour at room temperature and centrifuged. Subsequently 1.7 mol/l ammonium sulphate is added to the supernatant and slowly stirred for 2 hours at room temperature. Afterwards the precipitate is centrifuged off and homogenized in 0.2 1 dialysis buffer (15 mmol/l potassium phosphate, 50 mmol/l sodium chloride, pH 7.0) and dialyzed at 4C against $4 \times 10^1$ dialysis buffer. After centrifuging again the dialyzed product is purified on DE 52 CELLULOSE™ using dialysis buffer as the eluant.

The eluate is supplemented to a final concentration of 50 mmol/l potassium phosphate, Ph 7.5, 150 mmol/l sodium chloride (PBS), 0.1 % azide at a protein concentration of 15 mg/ml and loaded at room temperature onto a troponin T immunoadsorbent column and washed free of protein with PBS/0.1% azide. Subsequently it is eluted with 1 mol/l propionic acid.

The troponin T immunoadsorbent are prepared in that nitric acid and SPHEROSIL (Rhone Poulenc XOCOO5) washed with 15% water is after drying converted to Spherosil-NH2 with 10% (v/v) 3-(triethoxysilyl) propylamine in DMSO at 85° C. overnight. After the reaction the adsorbent is washed with DMSO and isopropanol and dried at 50° C.

Spherosil-NH2 is mixed with 10% glutaraldehyde solution, pH 3.7 and heated for 2 hours at 55C. The suspension is subsequently sucked off under a vacuum over a glass filter. Afterwards it is washed with redistilled water in a volume which is seven-fold that of SPHEROSIL™ and washed again with the five-fold volume of 10 mmol/l potassium phosphate, pH 8.0/0.1 mol/l sodium chloride. 10 mg troponin T per ml Spherosil in 10 mmol/l potassium phosphate, pH 8/0.1 mol/l sodium chloride, in ca 50% of the SPHEROSIL™ volume used, is then added per ml SPHEROSIL™ in a round-bottom flask. The flask is rotated overnight at room temperature on a rotary evaporator.

After filtration the SPHEROSIL™ is washed again several times with a 0.9% NaCl solution as well as with an ethanolamine solution. Afterwards 3 parts by volume ethanolamine solution are added and incubated for 1 hour at room temperature. After renewed filtration it is washed again with NaCl solution. Subsequently the immunoadsorber is adjusted to pH 7.5 with PBS and equilibrated with PBS/sodium azide. It is stored at 4C.

EXAMPLE 8

Determination of Myocardial Necrosis

An enzyme-immunoassay for the determination of human cardiac muscle troponin T is carried out according to Example 6 in the serum of 37 patients with symptoms of unstable angina pectoris.

A significant increase of troponin T was found in 13 of these patients (30%). This indicates that the determination of troponin T has a clearly higher sensitivity for the detection of the small infarction compared to the troponin I test.

In the transmural infarction the serum concentration curve of troponin T differs also significantly from that of troponin I. This is exemplified in FIG. 2, which shows the mean serum concentration curve for 52 patients with transmural myocardial infarction. In this infarction group troponin T as a mean is found to be increased for>300 hours after onset of pain. The time interval for the absolute diagnostic sensitivity in this group of patients lasts from the 6th –195th hour.

In a larger group of patients with very different infarct sizes (Q-wave and non-Q-wave AMI) the time interval of absolute diagnostic sensitivity of troponin T was from 12–140 hours after onset of pain.

Troponin T release shows the characteristics of both cytosolic and structurally bound marker proteins. In reperfused AMI a marked troponin T peak is found on day 1, which is absent in non-reperfused AMI (FIG. 3). The perfusion dependent change in early troponin T release can be used to predict non invasively the effectiveness of thrombolytic therapy. Similar results have not been shown for any other marker protein including troponin I.

General procedures for carrying out sandwich test assays are described in Narin, R. C. (ed.) (1980–1984) Practical Methods in Clinical Immunology Series, Churchill Livingstone, Edinburgh; and Weir D. M. (1985) Handbook of Experimental Immunology Vols. I & II, 4th edn., Blackwell Scientific Publications, Oxford, the disclosures of which are hereby incorporated by reference for such teachings.

General descriptions of processes for producing monoclonal antibodies are described in Milstein, C. "Monoclonal Antibodies" Sci. Am. 243 (4), 66–74 (1980; and Yelton, D. E. and Scharff M. D. "Monoclonal Antibodies: A Powerful New Tool in Biology and Medicine" Annu. Rev. Biochem. 50 657–680 (1981) the disclosures of which are hereby incorporated by reference for such teachings, and similar teachings for the production of polyclonal antibodies are described in Paul, J., Cell and Tissue Culture, 5th ed. New York: Churchill Livingstone (1975); Ham, R. G. "Clonal Growth of Mammalian Cells in a Chemically Defined, Synthetic Medium" Proc. Natl. Acad. Sci USA 53, 2880293 (1965); and Hayashi, I. et al "Hormonal Growth Control of Cells in Culture" In vitro 14, 23–30 (1978), disclosures of which are hereby incorporated by reference for such teachings.

The culturing of cell lines, and the isolation of monoclonal antibodies produced therfrom, are described in Milstein, C. "Monoclonal Antibodies" Sci. Am. 243 (4), 66–74 (1980); and Yelton, D. E. and Scharff M. D. "Monoclonal Antibodies: A Powerful New Tool in Biology and Medicine" Annu. Rev. Biochem. 50 657–680 (1981), the disclosures of which are hereby incorporated by reference for such teachings.

What is claimed is:

1. A method for the immunoassay determination of myocardial necroses in a patient, wherein detecting muscle injury can be accomplished for at least 150 hours after occurrence of an infarction, said method comprising:
   a) incubating a body fluid sample of the patient with
      i) at least one antibody to human cardiac muscle troponin T having cross-reactivity to human skeletal muscle troponin T which is less than 5% as determined by ELISA and cross-reactivity to troponin I and other myofibrillar proteins of less than 2% as determined by ELISA, and ii) a binding partner B for either human cardiac muscle troponin T or the antibody, wherein either the antibody or the binding partner B is labeled with a determinable group, to form an immunological complex containing the determinable group;

b) isolating the immunological complex from the remainder of sample; and c) determining the determinable group either in the isolated complex or in the sample remaining as an indicator of the human cardiac muscle troponin T in the sample;

thereby determining the occurrence of injury to a cardiac muscle of the patient.

2. Method of claim 1, wherein the body fluid is a serum or plasma sample.

3. Method of claim 1, wherein the binding partner B is a binding partner for troponin T, the immunoassay is a sandwich assay, and the complex containing the determinable group is a complex of said antibody, troponin T, and said binding partner.

4. Method of claim 1, wherein the binding partner B is a binding partner for the antibody, the immunoassay is a competitive assay, and the complex containing the determinable group is a complex of said antibody and the binding partner B.

5. Method of claim 1, wherein said incubation is with:

i) at least one first antibody to troponin T, and ii) a conjugate of at least one second, different antibody to troponin T and a determinable group.

6. Method of claim 1, wherein said incubation is with:

i) at least one antibody to troponin T, and ii) a conjugate of troponin T and a determinable group.

7. Method of claim 1, wherein the serum concentration of troponin T is monitored over at least a portion of the time interval of the 6th to the 195th hour after occurrence of pain arising from cardiac muscle injury.

8. Method of claim 1, wherein at least one antibody is a monoclonal antibody.

9. Method of claim 5 further comprising a plurality of phases including a solid phase and wherein said solid phase has immobilized to it either the antibody to troponin T or the binding partner B, an immunological complex forms during the incubation, the phases are separated to isolate the immunological complex, and the determinable group in one of the separated phases is determined.

10. Method of claim 5, wherein said first antibody is bound, either directly or indirectly, to a solid carrier.

11. Method of claim 10, wherein a first partner of a specific binding pair is conjugated to the first antibody, and a second partner of said specific binding pair is immobilized on a solid carrier.

12. Method of claim 11, wherein the antibody to human cardiac muscle troponin T to which is conjugated the first partner of said specific binding pair, the body fluid sample, and a conjugate of a second, different antibody to human cardiac muscle troponin T and the determinable group are simultaneously incubated in the presence of said solid carrier.

13. Method of claim 6 further comprising a plurality of phases including a solid phase and wherein said solid phase has immobilized to it either the antibody to troponin T or the binding partner B, an immunological complex forms during the incubation;

the phases are separated to isolate the immunological complex, and the determinable group in one of the separated phases is determined.

14. The method of claim 1 wherein the immunoassay is a sandwich assay and the binding partner B is an antibody or an antigen binding fragment thereof.

15. The method of claim 1 wherein the immunoassay is a competitive assay and the binding partner B is capable of binding to the anti-troponin-T antibody in competition with the troponin T in the sample.

16. Hybridoma cell line ECACC 89060901.

17. Hybridoma cell line ECACC 89030308.

18. Monoclonal antibody to human cardiac muscle troponin T produced from hybridoma cell line ECACC 89060901 or ECACC 89030308.

19. A kit for the immunoassay determination of myocardial necroses, comprising a) a first antibody to human cardiac muscle troponin T having a cross-reactivity to human skeletal muscle troponin T which is less than 5% as determined by ELISA and cross-reactivity to troponin I and other myofibrillar proteins of less than 2% as determined by ELISA, which first antibody is immobilized on a carrier or is immobilizable on a carrier after an immunological reaction, b) a second antibody to human cardiac muscle troponin T having a cross-reactivity to human skeletal muscle troponin T which is less than 5% as determined by ELISA and cross-reactivity to troponin I and other myofibrillar proteins of less than 2% as determined by ELISA, which second antibody is directly or indirectly conjugated to a determinable group, and c) the carrier, wherein the carrier has immobilized to it either the first antibody to troponin T or a member of a specific binding pair which member is an antibody which specifically binds to one of the antibodies which bind to troponin T or a member of a specific binding pair which specifically binds to its corresponding binding pair which is in turn conjugated to one of the antibodies which bind to troponin T.

20. The kit of claim 19, wherein the determinable group is an enzyme capable of causing a color-forming reaction, and the immunoassay determination is an enzyme immunoassay.

21. A kit for immunoassay determination of myocardial necroses in a patient, said kit comprising an antibody to human cardiac muscle troponin T, having a cross reactivity to troponin I and other myofibrillar proteins of less than 2% as determined by ELISA and cross reactivity to human skeletal muscle troponin T of less than 5% as determined by ELISA, and, in a separate container, a binding partner B for either human cardiac muscle troponin T or for said antibody, with one of said antibody and said binding partner being labeled with a determinable group.

22. A method for the immunoassay determination of myocardial necroses in a patient, wherein detecting cardiac muscle injury can be accomplished for at least 150 hours after occurrence of an infarction, said method comprising:

a) incubating a body fluid sample of the patient with i) at least one antibody to human cardiac muscle troponin T, and ii) a binding partner B for either human cardiac muscle troponin T or the antibody, wherein either the antibody or the binding partner B is labeled with a determinable group,
to form an immunological complex containing a determinable group; and b) determining the determinable group as an indicator of the human cardiac muscle troponin T in the sample to thereby determine the occurrence of injury to a cardiac muscle, wherein the at least one antibody to human cardiac muscle troponin T has a cross-reactivity to human skeletal muscle troponin T which is less than 5% as determined by ELISA and cross-reactivity to troponin I and other myofibrillar proteins of less than 2% as determined by ELISA.

23. A conjugate of an antibody to human cardiac muscle troponin T having a cross-reactivity to human skeletal muscle troponin T which is less than 5% as determined by ELISA and cross-reactivity to troponin I and other myofibrillar proteins of less than 2% as determined by ELISA, and a determinable group.

24. Conjugate of claim 23, wherein the determinable group is an enzyme which causes color development in the presence of a colorable substrate.

* * * * *